United States Patent [19]

Correia et al.

[11] Patent Number: 5,326,918

[45] Date of Patent: Jul. 5, 1994

[54] PURIFICATION OF 1,1-DICHLORO-1-FLUOROETHANE

[75] Inventors: Yves Correia, Chateau-Arnoux; Sylvain Perdrieux, Vernaison, both of France

[73] Assignee: Elf Atochem S.A., France

[21] Appl. No.: 147,512

[22] Filed: Nov. 5, 1993

[30] Foreign Application Priority Data

Nov. 18, 1992 [FR] France .................. 92 13851

[51] Int. Cl.$^5$ .................. C07C 17/38; C07C 19/02; C07B 63/00
[52] U.S. Cl. .................. 570/177; 204/158.11; 204/158.21; 570/179; 570/180
[58] Field of Search .................. 570/177, 180, 179; 204/158.21, 158.11

[56] References Cited

U.S. PATENT DOCUMENTS

| 3,218,363 | 11/1965 | Haszeldine | 260/648 |
| 3,844,914 | 10/1974 | Murchison | 204/158.2 |
| 4,948,479 | 8/1990 | Brooks et al. | 204/158.21 |
| 5,105,035 | 4/1992 | Wang et al. | 570/177 |
| 5,175,380 | 12/1992 | Raab | 570/177 |
| 5,190,626 | 3/1993 | Yates et al. | 204/158.21 |
| 5,198,593 | 3/1993 | Kishita et al. | 570/177 |

FOREIGN PATENT DOCUMENTS

| 177645 | 3/1979 | Czechoslovakia . |
| 0420709 | 4/1991 | . |
| 4305537 | 10/1992 | Japan | 570/177 |
| 5032567 | 2/1993 | Japan | 570/177 |

OTHER PUBLICATIONS

Chemical Abstract, vol. 93, No. 3, Jul. 21, 1980; Abstract No. 93:25891z, Vaclav Dekek et al., "Refining of technical 1,1,2-trifluorotrichloroethane".

Primary Examiner—Joseph E. Evans
Attorney, Agent, or Firm—Morgan & Finnegan

[57] ABSTRACT

This invention relates to a process to remove the unsaturated impurities (in particular vinylidene chloride) present in a crude 1,1-dichloro-1-fluoroethane. This process comprises subjecting the product to be purified, in the liquid phase, in the presence of oxygen, to an irradiation by short wavelength UV rays (200 to 360 nm), then washing with an alkaline and/or reducing solution, and drying.

9 Claims, No Drawings

PURIFICATION OF 1,1-DICHLORO-1-FLUOROETHANE

FIELD OF THE INVENTION

The present invention relates to the field of chlorofluorinated hydrocarbons and more particularly to a process for the purification of 1,1-dichloro-1-fluoroethane. This compound, also called HCFC-141b, is particularly advantageous as a substitute for chlorofluorocarbons (CFC) in various applications, especially for defluxing printed circuits and manufacturing polymer foams.

BACKGROUND OF THE INVENTION 1,1-Dichloro-1-fluoroethane, prepared by fluorination of Vinylidgne chloride (A. E Feiring, J. Fluorine Chem., 1979, 14(1), 7–18)or of 1,1,1-trichloroethane (U.S. Pat. No. DE 2,137,806), contains, as impurities, chlorinated or chlorofluorinated unsaturated compounds which are undesirable when 1,1-dichloro-1-fluoroethane is used and must therefore be removed. Among the unsaturated impurities, the most harmful is vinylidene chloride, whose boiling point (31.7° C.) is too close to that (32° C.) of 1,1-dichloro-1-fluoroethane for its separation to be possible by distillation.

Among the various techniques already proposed for removing the unsaturated impurities (in particular vinylidene chloride ) present in 1,1-dichloro-1-fluoroethane, there may be mentioned:

liquid phase photochlorination (U.S. Pat. No. 4,948,479 ) or vapour phase photochlorination (publication WO 92/10452)

chlorination in the presence of a Lewis acid catalyst (publication EP 0,420,709)

absorption of the impurities on a carbonaceous molecular sieve (U.S. Pat. No. 4,940,824) or on active charcoal (U.S. Pat. No. 4,950,816)

catalytic hydrogenation (U.S. Pat. No. 5,105,035)

treatment with concentrated $H_2SO_4$ (publication JP 04-99737 ).

It has now been found that the unsaturated impurities, in particular vinylidene chloride, may be removed by photooxidation.

DESCRIPTION OF THE INVENTION

The subject of the invention is thus a process for the purification of a 1,1-dichloro-1-fluoroethane containing unsaturated impurities, characterized in that the product to be purified in the liquid phase is subjected, in the presence of oxygen, to an irradiation by short-wavelength UV rays (200 to 360 nm), then washed with an alkaline and/or reducing solution, and dried.

A crude 1,1-dichloro-1-fluoroethane to be purified generally contains less than 1000 ppm of vinylidene chloride and several tens of ppm of other unsaturated impurities such as, for example, 1-chloro-1-fluoroethylene and dichloroacetylene. However, the process according to the invention also applies to the treatment of a 1,1-dichloro-1-fluoroethane in which the unsaturated impurities contents are much greater than those mentioned above, as well as to the treatment of a 1,1-dichloro-1-fluoroethane containing, in addition to unsaturated impurities, a small proportion if saturated organic compounds such as, for example, pentafluorobutane (up to 0.2 %) and 1,1,1-trichloroethane (up to 200 ppm).

The photooxidation according to the invention is carried out at a temperature between 0° and 50° C., preferably between approximately 20° and 30° C., at a pressure sufficient (generally 1 to 5 bars absolute) for the 1,1-dichloro-1-fluoroethane to be purified to be in the liquid phase.

The short-wavelength UV rays, which are the only effective ones, may be supplied by any known means, in particular by a moderate pressure mercury lamp containing a quartz wall, which delivers most of its irradiation at 254 nm. The irradiation power may be between 5 and 40, preferably between 13 and 20 kilowatts per $m^3$ of liquid to be purified.

The oxygen required for the photooxidation may be introduced continuously or noncontinuously into the liquid to be purified. The molar amount of oxygen to be used must be at least equal to the number of moles of unsaturated impurities present in the 1,1-dichloro-1-fluoroethane to be purified, and preferably 5 to 10 times greater. Dilution of the oxygen with nitrogen does not harm the efficiency of the treatment; it is thus possible to use air in place of pure oxygen.

The duration of the photooxidation treatment may vary within wide limits (generally from 30 minutes to 5 hours, preferably from 1 to 3 hours). It obviously depends not only on the initial unsaturated impurities content in the 1,1-dichloro-1-fluoroethane to be purified and on the operating conditions used, but also on the desired efficiency which may easily be controlled by withdrawing samples and analyzing them by chromatography.

After this treatment, the 1,1-dichloro- 1-fluoroethane is washed so as to remove the products formed by the photooxidation and consisting essentially of phosgene, hydrochloric acid, formaldehyde, monochloroacetyl chloride and possibly dichloroethylene peroxide. This washing, which may be carried out continuously or noncontinuously, is carried out by bringing the 1,1-dichloro-1-fluoroethane into intimate contact with an aqueous alkaline and/or reducing solution such as, for example, an aqueous solution of sodium hydroxide, of ammonia, of hydrazine or of alkali metal sulphite or bisulphite. It is advantageous to use a large excess of alkaline and/or reducing agent and then to rinse the 1,1-dichloro-1-fluoroethane with neutral water. The excess of alkaline and/or reducing agent may range from 5 to 100 times (preferably approximately 20 times) the amount of acid functional groups generated by the photooxidation.

The final drying of the 1,1-dichloro-1-fluoroethane thus purified may be carried out by any known means, for example by bringing into contact with a molecular sieve, a siliporite or calcium sulphate.

EXAMPLES

The following examples illustrate the invention without limiting it. The contents mentioned are expressed by weight.

EXAMPLE 1

500 ml of 1,1-dichloro-1-fluoroethane containing 313 ppm of vinylidene chloride ($VC_2$) are placed in a glass container and then illumination is carried out in the liquid phase with UV rays supplied by a tenth of the surface area of a 75-watt medium-pressure Hanau quartz lamp which mostly radiates at 254 nm. The illumination is carried out at atmospheric pressure and at 25° C., while bubbling oxygen into the liquid, the oxygen flow rate being approximately 100 ml/hour.

In the course of time, liquid samples are withdrawn and the VC$_2$ concentrations are measured by gas phase chromatography, after washing by means of an aqueous solution containing 5% of sodium sulphite and 2% of sodium hydroxide.

After exposure for one hour, the VC$_2$ content is now only 17 ppm. It is less than 5 ppm after exposure for 2 hours.

EXAMPLE 2 ( COMPARATIVE )

The reaction is carried out as in Example 1, but replacing the Hanau lamp by a 75-watt glass-wall lamp of the neon sign type shining in the blue region (approximately 400 run). By illuminating the liquid with a tenth of the surface area of the lamp, the following results were obtained:

| Exposure time (hours) | 0 | 1.5 | 4 | 7 |
|---|---|---|---|---|
| VC$_2$ content (ppm) | 310 | 295 | 280 | 265 |

After 7 hours, the VC$_2$ content has only decreased by approximately 5%.

EXAMPLE 3 (COMPARATIVE)

The reaction is carried out as in Example 1, but replacing the oxygen with nitrogen. The following results are obtained:

| Time (hours) | 0 | 1 | 2 | 3 | 5 | 8 |
|---|---|---|---|---|---|---|
| VC$_2$ content (ppm) | 314 | 172 | 146 | 125 | 77 | 25 |

Gas phase chromatographic analysis of the samples withdrawn shows the presence of significant amounts (200 to 600 ppm) of dimerization products: C$_4$H$_5$F$_2$Cl$_3$ and C$_4$H$_6$F$_2$Cl$_2$. In Example 1, these products only appear in a negligible amount (less than 1 ppm).

EXAMPLE 4

200 l/hour of 1,1-dichloro-1-fluoroethane, containing 320 ppm of VC$_2$ and 1200 ppm of other saturated organic derivatives, and 150 l/h of oxygen are introduced continuously into a stirred, 400 liter reactor equipped with a 6-kilowatt mercury vapour UV lamp (quartz casing). The reaction mixture is maintained at 25°–28° C. and at atmospheric pressure.

Analysis of the liquid at the reactor outlet shows that it now contains only 35 ppm of VC$_2$; its peroxides content (expressed in H$_2$O) is 5 mg/kg, its acidity (expressed in HCl) is 30 mg/kg and its phosgene content is 15 mg/kg.

This liquid is then intimately mixed with 1500 l/hour of a 0.7 mol/liter aqueous ammonia solution in a column packed with Pall Inox rings and the mixture is then settled continuously. The aqueous phase is recycled to the column and the organic phase is washed continuously with 2000 l/hour of neutral water in a column packed with Pall Inox rings.

The flow of thus washed 1,1-dichloro-1-fluoroethane is finally dried continuously on a bed of 400 liters of a 3 Å molecular sieve. At the dryer outlet, the 1,1-dichloro-1-fluoroethane now contains only 20 ppm of water and is free from peroxides, phosgene and acidity.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the purification of a 1,1-dichloro-1-fluoroethane containing unsaturated impurities, comprising subjecting the product to be purified in the liquid phase, in the presence of oxygen, to an irradiation by short-wavelength UV rays between about 200 to about 360 nm, then washing with an alkaline and/or reducing solution, and drying.

2. Process according to claim 1, wherein the photooxidation is carried out at a temperature between 0 and 50° C.

3. Process according to claim 1, wherein the irradiation power is between 5 and 40 kilowatts per m$^3$ of liquid to be purified.

4. Process according to claim 1, wherein the molar amount of oxygen used is at least equal to the number of moles of unsaturated impurities present in the 1,1-dichloro-1-fluoroethane to be purified.

5. Process according to claim 1, wherein, after irradiation, the 1,1-dichloro-1-fluoroethane is washed with an aqueous solution of sodium hydroxide, of ammonia, of hydrazine or of alkali metal sulphite or bisulphite.

6. Process according to claim 1, wherein the treatment is carried out continuously.

7. Process according to claim 2, wherein the temperature is between approximately 20° and 30° C.

8. Process according to claim 3, wherein the irradiation power is between 13 and 20 kilowatts per m$^3$ of liquid to be purified.

9. Process according to claim 4, wherein the molar amount of oxygen used is 5 to 10 times greater.

* * * * *